(12) United States Patent
Jiang

(10) Patent No.: US 6,870,612 B2
(45) Date of Patent: Mar. 22, 2005

(54) PORTABLE SPECTRAL IMAGING MICROSCOPE SYSTEM

(75) Inventor: Yanan Jiang, West Lafayette, IN (US)

(73) Assignee: SpectraCode, Inc., West Lafayette, IN (US)

(*) Notice: Subject to any disclaimer, the term of this patent is extended or adjusted under 35 U.S.C. 154(b) by 104 days.

(21) Appl. No.: 10/346,540

(22) Filed: Jan. 17, 2003

(65) Prior Publication Data

US 2003/0142302 A1 Jul. 31, 2003

Related U.S. Application Data

(60) Provisional application No. 60/350,847, filed on Jan. 22, 2002.

(51) Int. Cl.[7] .............................. G01J 3/44; G01N 21/65
(52) U.S. Cl. ...................................................... 356/301
(58) Field of Search ................................. 356/301, 317, 356/318, 326, 328; 250/458.1, 459.1, 461.1, 461.2

(56) References Cited

U.S. PATENT DOCUMENTS

| | | |
|---|---|---|
| 5,194,912 A | 3/1993 | Batchelder et al. |
| 5,442,438 A | 8/1995 | Batchelder et al. |
| 5,479,252 A | 12/1995 | Worster et al. |
| 5,510,894 A | 4/1996 | Batchelder et al. |
| 5,623,342 A | 4/1997 | Baldwin et al. |
| 6,002,476 A | 12/1999 | Treado |
| 6,008,894 A | 12/1999 | Schmucker et al. |
| 6,069,690 A | 5/2000 | Xu et al. |
| 6,115,528 A | 9/2000 | Schmucker et al. |
| 6,310,686 B1 | 10/2001 | Jiang |
| 6,403,947 B1 | 6/2002 | Hoyt et al. |
| 6,503,478 B2 | 1/2003 | Chaiken et al. |
| 6,545,755 B1 | 4/2003 | Ishihama et al. |

*Primary Examiner*—F. L. Evans
(74) *Attorney, Agent, or Firm*—Brinks Hofer Gilson Lione

(57) ABSTRACT

A portable spectral imaging microscope includes a probe head coupled via fiber optic cabling to a laser source and to a spectrograph. The probe head is coupled to a position controller that is mounted on a base suitable for positioning adjacent to a sample. The position controller has five degrees of freedom that permits one to adjust the position and direction of the probe head relative to the sample over a wide range of dimensions and angles. The entire probe head can be easily moved in order to precisely align the objective lens to stationary samples for simultaneous viewing and spectral analysis.

36 Claims, 3 Drawing Sheets

PORTABLE SPECTRAL IMAGING MICROSCOPE SYSTEM

CROSS-REFERENCE TO RELATED APPLICATIONS

The present application is related to U.S. Provisional Application Ser. No. 60/350,847 filed Jan. 22, 2002, which is hereby incorporated by reference.

BACKGROUND OF THE INVENTION

1. Field of the Invention

The present invention generally relates to portable spectroscopic imaging microscopes, including portable Raman imaging microscope systems and portable fluorescence imaging microscope systems.

2. Description of Prior Art

Conventional spectral microscope systems allow a sample to be viewed through a video camera or an eyepiece. However, the sample must generally be fixed on a movable stage or table of the microscope and moved toward or away from the objective lens to achieve proper focus as disclosed, for example, in U.S. Pat. Nos. 5,194,912; 5,442,438; 5,479,252; 6,002,476 and 6,069,690. For some applications, such as samples in a vacuum chamber, in an oven, or located in a manufacturing process, one cannot use such conventional spectral microscope systems. U.S. Pat. No. 6,008,894 discloses a Raman spectroscopy probe for analyzing specimens in adverse environments requiring remote focusing of the probe, and suggests mounting the probe to achieve nanometer positional variations. U.S. Pat. No. 6,115,528 discloses a fiber optic based probe assembly for use in hostile environments, but the probe heads do not allow the sample to be directly viewed and thus do not allow the collection of either a single or multiple spectra from precisely identified locations within a sample, as visually viewed through the same objective lens used to collect the spectra. One system that does allow the collection of either a single or multiple spectra from precisely identified locations within a sample, as visually viewed through the same objective lens used to collect the spectra is disclosed in my earlier U.S. Pat. No. 6,310,686, which does suggest manual and machine-powered manipulation of a probe head containing the objective lens, but required spacing from the sample by less than 1 cm and did not disclose any mechanism for accurately positioning the probe head.

Despite the variety of spectral microscopic systems that have been developed, there remains a need for a portable spectroscopic microscope system that is easily adapted to a variety of work environments and allows the simultaneous observation of the sample and acquisition of spectral information from the sample. There is a further need for a spectroscopic microscope system that can be used any angle and is sufficiently portable to be brought to a stationary sample rather than requiring that the sample be set on a translation stage for alignment to a fixed microscope objective. There is particularly a need for a portable spectroscopic microscope system having the forgoing mobility that requires no optical realignment upon movement of the system from one position to another.

BRIEF SUMMARY OF THE INVENTION

The forgoing needs are met by a spectroscopic microscope of the present invention. The microscope system comprises a source of spectral energy, typically taking the form of a laser that is coupled to a probe head containing an objective lens system for directing spectral energy from the source toward a sample. The coupling can include fiber optic elements, spatial filters, band pass filters, lenses, mirrors, and other optical transmission elements defining an optical path between the source of spectral energy and the objective lens. Any of the elements forming the optical path between the source of spectral energy and the objective lens can be included in the probe head. The spectral energy can take the form of white-light and/or expanded laser light.

The microscope system also comprises collection elements coupled to the objective lens for receiving energy returned from the sample. The collection elements can also be located in the probe head and include an optical image collection device coupled to the collection elements for extracting a visual image of the sample. The optical image collection device can comprise a lens, a mirror, and a CCD camera driven by known software to produce a signal that can be supplied to a visual monitor for real-time optical observation and evaluation of the sample. For example, the visual image can be derived from a built-in video camera for viewing the sample that can take the form of either with a video monitor or CRT, or by using video frame grabbing software on a computer, such as a conventional PC.

The microscope system also comprises a spectral collection device that is coupled to the collection elements for extracting a spectral characteristic of the sample. The spectral collection device can include a lens system, a spatial filter, a Rayleigh rejection filter, fiber optic elements and a spectrograph, preferably one capable of collecting Raman spectrographic information from the sample. Any of the elements of the spectral collection device can be included in the probe head so that movement of the probe head achieves coordinate movement of the location of the spectral characteristic extraction.

The spectroscopic microscope system of the present invention also comprises a base that is adapted to be situated adjacent to a sample for supporting the probe head containing at least some of the forgoing optical components above any convenient substrate in the vicinity of the sample. A position controller is coupled to the base and the probe head for adjusting the position of the objective lens and related optical components with respect to the sample. The relative position of the objective lens is ascertained at least in part by observation of the visual image of the sample derived from the optical image collection device.

The source of spectral energy, which generally takes the form of a laser, and the spectrograph are coupled to the probe head by fiber optic cabling. The characteristics of these components, such as laser wavelength, bandwidth, power and spectrograph focal length, grating groove density, spectral resolution, spectral window and optical design, can be custom tailored to the specific needs of the samples to the tested. The probe head position is adjustable for alignment to stationary samples. The probe head can also be used at any angle, vertically and horizontally. The probe head can have a working distance from the sample of up to about 2.5 cm, so one can use the present invention to look through windows in vacuum systems, oven or gas handing systems, etc. The magnification and working distance of the probe head can be changed by replacing the objective lens system much as is done in conventional microscopes, using standard or custom microscope objectives.

One of feature of a spectroscopic microscope of the present invention is that it incorporates both spectral and video image collection optics which are contained in a common probe head and both coupled to the sample through the same objective lens. Thus observation of the sample and acquisition of spectra can be performed simultaneously. Further any change of position of the probe that might affect a change in the spectra from the sample is automatically tracked by the video image.

A further feature of spectroscopic microscope of the present invention is that it can be used any angle and brought to a stationary sample rather than requiring that the sample be set on a translation stage for alignment to a fixed microscope objective. Furthermore, when implemented using a collection fiber bundle containing multiple optical fibers (and an imaging spectrograph with sufficient resolution to separately view each fiber), a spectroscopic microscope of the present invention can be used to simultaneously collect multiple spectra, each originating from a different precisely defined location within the video field of view.

The spectroscopic microscope of the present invention differs from a fiber coupled probe head used for collecting Raman spectra for industrial and laboratory process monitoring since the spectroscopic microscope of the present invention allows direct viewing of the sample from which spectra are collected. This is due to the fact that the spectroscopic microscope of the present invention includes built-in video camera that makes it possible to visually align the objective and thus insure that spectra are collected from a precisely identified region in a sample.

These and other features and advantages of the present invention will become apparent to those skilled in the art from a consideration of the following description of a preferred embodiment of the present invention that is shown in the accompanying drawings.

DETAILED DESCRIPTION OF THE PREFERRED EMBODIMENTS

Figure 1:
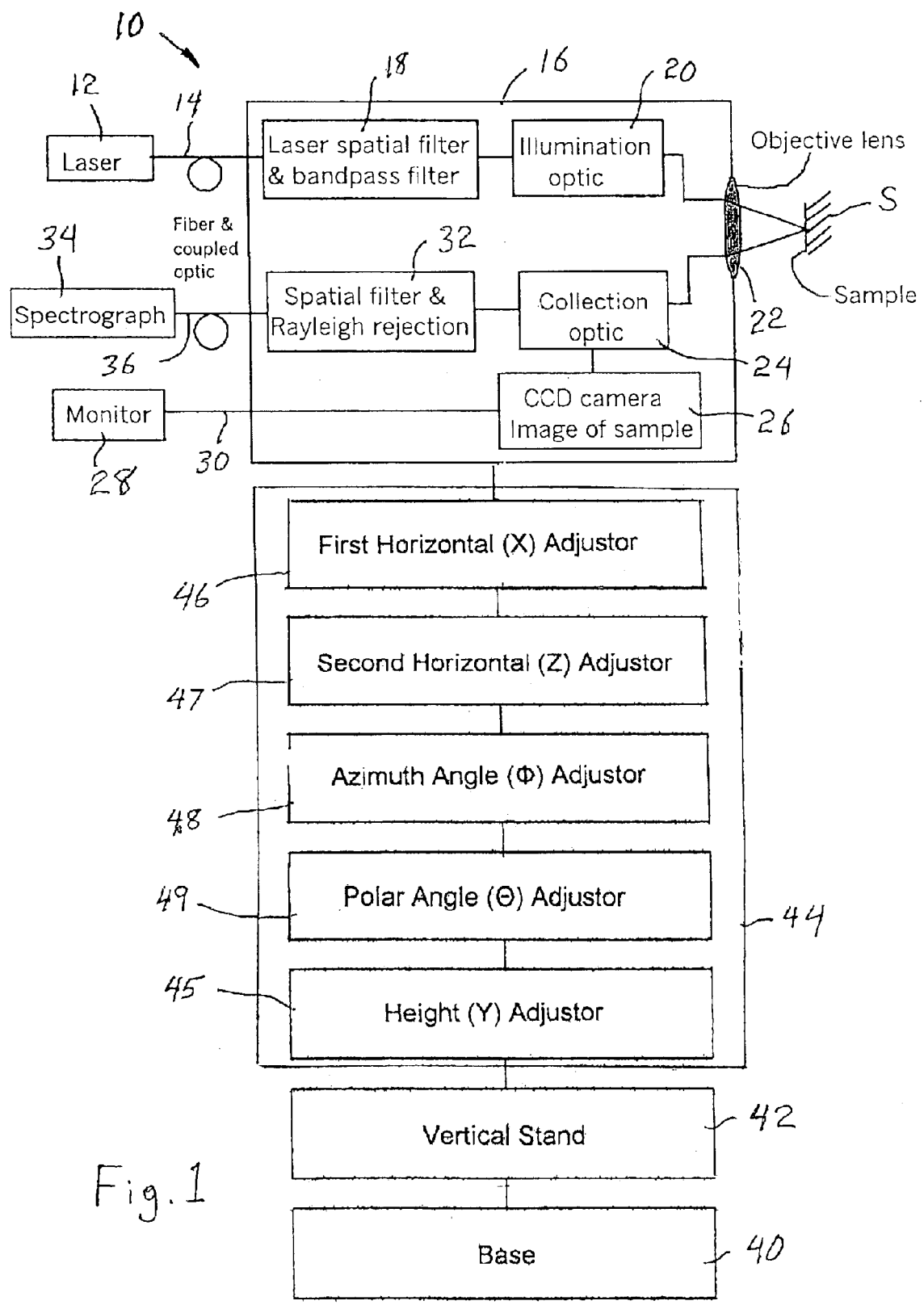
FIG. 1 is a block diagram of the functional elements of spectroscopic microscope of the present invention.

A portable spectroscopic imaging microscope system 10 of the present invention is shown in block diagram form in FIG. 1. The system 10 includes a laser 12 coupled by a fiber optic cable 14 to a probe head 16. The probe head 16 includes filter elements 18 and optical path defining elements 20 that direct energy from the fiber optic cable 14 to an objective lens 22 to illuminate a specimen or sample S. The probe head also includes collection optical path defining elements 24 that are arranged to intercept any desired spectral signal reflected, scattered or emitted by the illuminated sample S passing back through the objective lens 22. The collection optic elements 24 direct a portion of the reflected, scattered or emitted signal to a CCD camera 26 to form a visual image signal of the sample S. The visual image signal is transmitted to a monitor 28 by way of a suitable cable 30. The collection optics 24 also direct a portion of the reflected, scattered or emitted signal to filter elements 32 designed to allow only a desired band width of energy through to a spectrograph 34 that is coupled to the collection optics 24 in the probe head 16 by fiber optic cable 36.

The system 10 also includes a base 40 that can be positioned on any underlying substrate so as to be situated conveniently close to the specimen S. The base 40 generally supports a stand 42 that is generally vertical and defines a vertical or polar axis. A position controller 44 can be coupled to the base 40, or the vertical stand 42, and to the probe head 16 to permit the probe head 16 to be situated any desired location and aimed in any direction relative to the specimen S. The position controller 44 includes a height adjustor 45 that is capable of moving the probe head 16 vertically through a distance Y of 10 cm or more. The position controller 44 can also include first and second horizontal adjusters 46 and 47 that are capable of moving the horizontally through distances X and Z of 10 cm or more with micrometer accuracy. The position controller 44 can also include an azimuth angle adjuster 48 that can tilt the probe head 16 through an azimuth angle φ relative to the vertical or polar axis through a range of at least 45°. The position controller 44 can also include a polar angle adjuster 49 that can rotate the probe head 16 through a polar angle Θ relative to the base of at least 45°.

Figure 2:
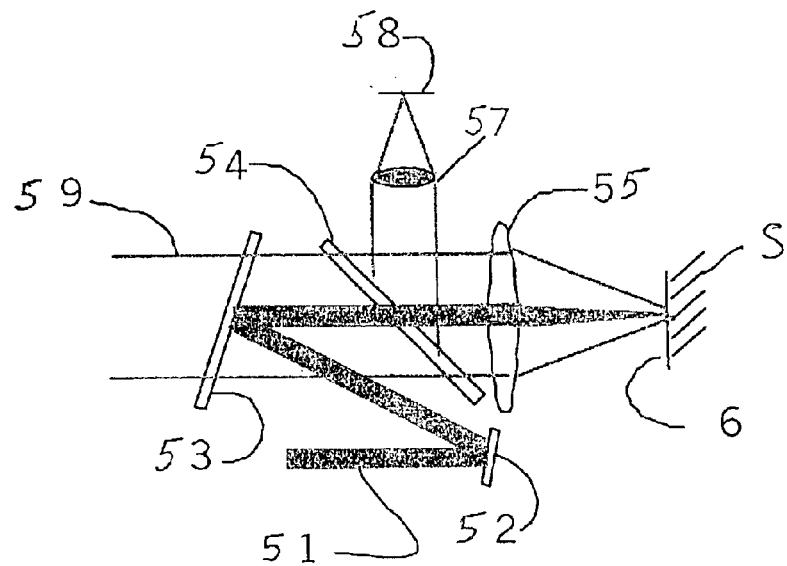
FIG. 2 and FIG. 3 are ray diagrams of two possible implementations of the illumination, collection and video camera optics of the present invention.
Figure 3:
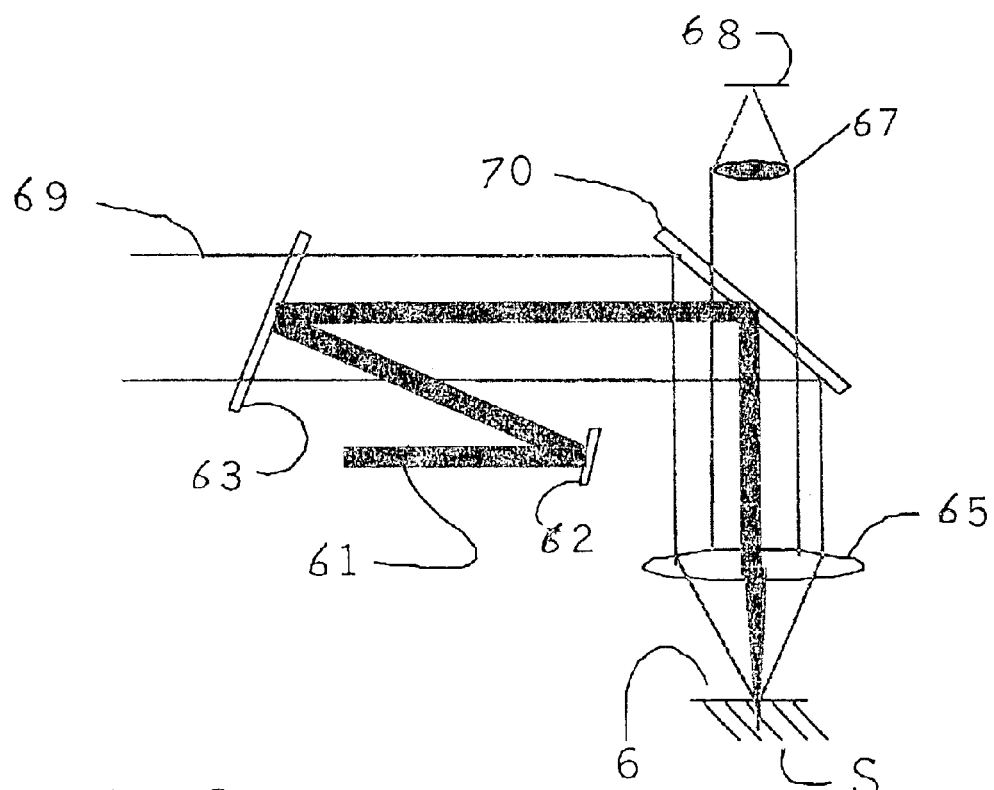

FIGS. 2 and 3 show two alternative optical arrangements that can be employed in the probe head 16. Additional optical arrangements are possible and FIGS. 2 and 3 are intended to merely be exemplary. In FIG. 2, an illuminating collimated beam of light 51 travels from a source, not shown, toward a mirror 52, which redirects the illuminating beam 51 toward a small area at the center of a holographic notch filter or dichroic optical filter 53. The illuminating beam is again reflected by the filter 53 along a principal axis of the probe head 16 through a beam splitter 54. The beam splitter 54 can be a long-pass filter to transmit laser and spectral light while reflecting shorter wavelength light. The illuminating beam is preferably in the visible or near infrared region of the spectrum, and so continues in a straight line through the beam splitter 54 toward the objective lens system 55 that focuses the illuminating beam on a selected portion 6 of the sample or specimen S. The exact location of the selected portion 6 and the angle of incidence of the illuminating beam on the specimen S is determined by the position controller 44 shown in FIG. 1. Additionally, the direction of the principal axis of the probe head 16 is also determined by the position controller 44.

As a consequence of the illumination of the specimen S by the illuminating beam, the specimen S reflects, scatters or emits some of the energy at the same or longer wavelength. Some of this reflected, scattered or emitted light is collected by the objective lens system 55 and directed back toward the beam splitter 54, which reflects the shorter wavelength light and a small percentage of the laser light toward the input lens 57 of a video camera 58 that allows one to directly view the sample and focal spot of laser. The specimen S also reflects, scatters or emits some of the energy in the longer wavelength infrared spectral region of the spectrum. This spectral region is of particular interest as it is characteristic of molecular vibrational fundamentals of the various materials that form the specimen S. Some of this longer wavelength light is collected by the objective lens system 55 and directed back through the beam splitter 54. To achieve this, the beam-splitter 54 can be either a long-pass filter that will transmit longer wavelength spectral light like Raman spectra and fluorescence while reflecting shorter wavelength light. The beam-splitter 54 can also be an anti-reflective coating beam-splitter to transmit the laser and spectral light of interest while reflecting a small percentage of light to the video camera 58. The longer wavelength light continues through the filter 53, which acts to exclude a wide range of wavelengths that are undesirable, leaving merely the wavelengths of interest 59 which can be directed to a suitable instrument for spectral analysis.

In the arrangement shown in FIG. 3, an illuminating collimated beam of light 61 travels from a source, not shown, toward a mirror 62, which redirects the illuminating beam 61 toward a small area at the center of a holographic notch filter or dichroic optical filter 63 in a manner similar to FIG. 2. The illuminating beam 61 is again reflected by the filter 63 along a principal axis of the probe head 16 to a beam splitter 70. The beam splitter 70 can be either a short-pass filter to reflect laser and spectral light while transmitting shorter wavelength light and small percentage laser light or a neutral reflective beam splitter to reflect laser and spectral light while transmitting a small percentage of light. The illuminating beam 61 is redirected along a second principal axis of the probe head 16 toward the objective lens system 65 that focuses the illuminating beam on a selected portion 6 of the sample or specimen S. Again, the exact location of the selected portion 6 and the angle of incidence of the illuminating beam 61 on the specimen S can, be determined by a position controller 44 as shown in FIG. 1.

Some of the reflected, scattered or re-emitted light is collected by the objective lens system 65 and directed back through the beam splitter 70 to the input lens 67 of a video camera 68 that allows one to directly view the sample and focal spot of the illuminating beam 61. Some longer wavelength light is collected by the objective lens system 65 and directed back to the beam splitter 70 where it is redirected back along the first principal axis of the probe head 16. The longer wavelength light again continues through the filter 63, which acts to exclude a wide range of wavelengths that are undesirable, leaving merely the wavelengths of interest 69 which can be directed to a suitable instrument for spectral analysis. Since the direction of the principal axis of the probe head 16 is determined by the position controller 44, the point from which the reflected, scattered or re-emitted light is collected by the objective lens system 65 is also determined by the position controller 44 of FIG. 1.

Figure 4:
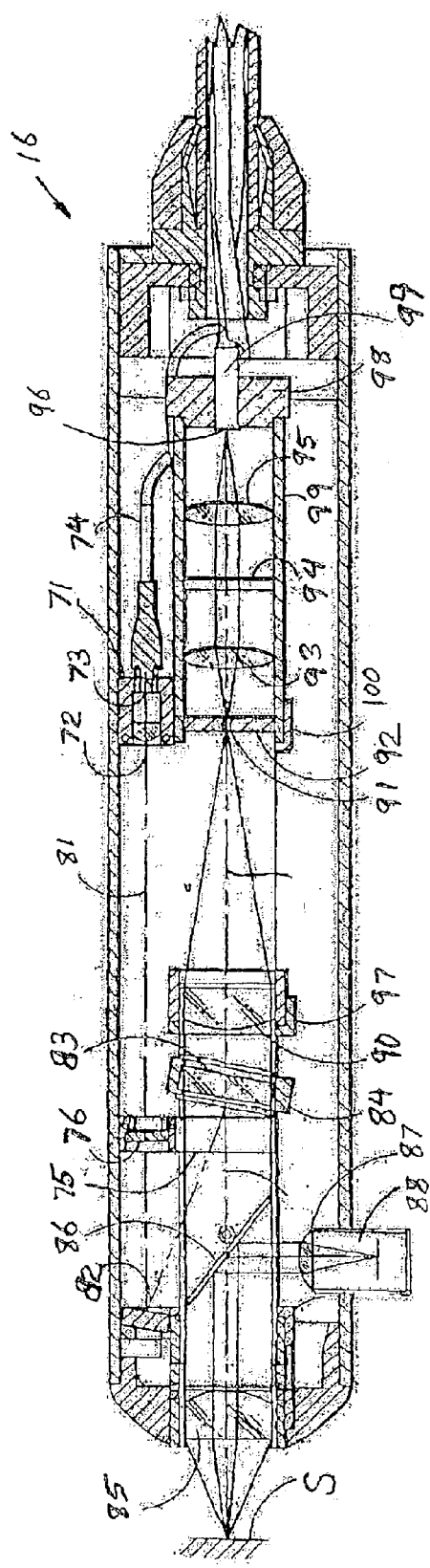
FIG. 4 is a sectional view of a probe head suitable for use in the present invention.

One commercially available probe head 16 is shown in FIG. 4. Light of the correct laser source wavelength starts at the exit end 73 of optical fiber 74 in support 71, and is collimated by lens 72. The collimated laser beam 81 passes through the band-pass filter 76 in support 75. The band-pass filter 76 controls the wavelength deviation of the source light 81 directed toward the sample S. After passing the band-pass filter 76, the collimated laser beam 81 reflects off of mirror 82 toward filter 83 in support 84. The optical filter 83 can be an interference filter or long pass filter designed to highly reflect wavelengths of the laser beam 81 and transmit light having a wavelength longer than the laser source. Alternatively, the optical filter 83 can be a holographic notch filter designed to highly reflect wavelengths of the laser beam 81 and transmit light having a wavelength that is either longer or shorter than the laser source. The reflective character of the filter 83 highly reflects the laser light beam 81 toward the objective lens system 85 and toward the sample S. The monochromatic laser light is scattered by the sample S creating a Raman signal that is typically about 1 part in 1 million of the reflected and scattered incident light.

The Raman spectrum appears as light that is shifted to longer wavelength from the source laser beam 81. The observed wavelength shifts are produced by molecular vibrational fundamentals of the various materials found in the sample S. The portion of scattered, reflected, and Raman or fluorescence light are collected and recollimated by the same objective lens 85 and directed parallel to the optical axis P of the probe head through the beam splitter 86. The beam splitter 86 reflects a small percentage of the collected and recollimated light to video camera lens 87 in video camera 88. The video camera 88 allows direct viewing of the sample S and focal spot of the laser beam 81 on the sample. Most of the collected and recollimated light is transmitted by the beam splitter 86 toward the filter 83. Filter 83 rejects substantially all of the source laser light and transmits Raman scattering or fluorescence light, which have a longer wavelength than the source laser.

Still, some un-rejected light at about the wavelength of the source laser beam 81 is usually able to pass through filter 83. The un-rejected light of about the wavelength of the source laser coming through filter 83 can swamp some details of the Raman or fluorescence signal. A focusing lens 90 held by support 97 projects an image of the recollimated beam from the sample S into an aperture 91 at an entrance end 92 of spatial filter 100. The spatial filter 100 acts to further extinguish the un-rejected light at about the wavelength of the source laser beam 81. Within the spatial filter 100, a first lens 93 is positioned to focus on the aperture 91, so that any radiation passing through the aperture 91 is again collimated within spatial filter housing 99. An interference filter or holographic notch filter 94 is selected to further reflect light at the laser wavelength and transmit Raman or fluorescence signals. A second lens 95 collects the signal passing through the filter 94 and focuses the signal on an entrance end 96 of optical fiber bundle 97 held in holder 99. The fiber bundle 97 carries the Raman or fluorescence signal to the spectrograph and detector, not shown.

Thus both the initial illuminating laser beam 81 and the recollimated beam transmitted by the beam splitter 86 toward the filter 83 are aligned with the axis P of the probe head 16. Any movement of the probe head 16 has the effect of moving both the focal point of the illuminating beam 81, and the area from which scattered and reflected light are collected and recollimated by the objective lens system 85. Further, despite any movement of the probe head, the collected and recollimated light still travels parallel to the probe head axis P. Thus, the illumination and collection of information from a specimen S can be controlled by the control of a single position controller 44. This enables the probe head 16 to be brought to the sample S rather than requiring the sample to be set on a translation stage for alignment to a fixed microscope objective as was commonly the practice with the prior art. Since the probe head 16 incorporates both spectral and video image collection optics coupled to the sample through the same objective lens, the built-in video camera 88 makes it possible, using the position controller 44 of FIG. 1, to visually align the objective lens system 85 and the principal axis X to the precise region of a sample S for spectral collection. A variety of readily interchangeable standard microscope objectives can be employed to better control the focusing.

Although the invention has been described in detail with reference to a preferred embodiment, variations and modifications exist within the scope and spirit of the invention as described and defined in the following claims.

What is claimed is:

1. A spectroscopic microscope for evaluating a characteristic of a sample, the microscope comprising: a source of spectral energy, a probe head having an objective lens for directing spectral energy from the source toward said sample, optical transmission elements within the probe head defining an optical path between the source of spectral energy and the objective lens, collection elements within the probe head coupled to the objective lens including an optical filter for receiving energy returned from the sample, an optical image collection device coupled to the collection elements for extracting a visual image of the sample from energy reflected from the optical filter, a spectral collection device coupled to the collection elements for extracting a spectral characteristic of the sample from energy passing through the optical filter, a base adapted to be situated adjacent to the sample and a position controller coupled to the base and the probe head for adjusting the position of the objective lens with respect to the sample, the relative position being ascertained at least in part by observation of the visual image of the sample derived from the optical image collection device.

2. The spectroscopic microscope of claim 1 wherein the base comprises a stand and a support for supporting the stand in a vertical orientation defining a polar axis.

3. The spectroscopic microscope of claim 2 wherein the position controller comprises a first angle adjustment means for adjusting the azimuth angle Φ of the probe head relative to the polar axis through a range of at least 45°.

4. The spectroscopic microscope of claim 3 wherein the position controller comprises a second angle adjustment means for adjusting the polar angle Θ of the probe head relative to the base through a range of at least 45°.

5. The spectroscopic microscope of claim 2 wherein the position controller comprises a vertical (Y) adjustment means for adjusting the vertical position of the probe head relative to the base by a distance of at least 10 cm.

6. The spectroscopic microscope of claim 5 wherein the position controller comprises a first horizontal (X) adjustment means for adjusting the horizontal position of the probe head in a first horizontal direction relative to the base by a distance of at least 10 cm.

7. The spectroscopic microscope of claim 6 wherein the position controller comprises a second horizontal (Z) adjustment means for adjusting the horizontal position of the probe head in a second horizontal direction relative to the base by a distance of at least 10 cm.

8. The spectroscopic microscope of claim 1 wherein the optical transmission elements within the probe head defining an optical path between the source of spectral energy and the objective lens comprises at least one of: a spatial filter, a band pass filter, a lens, and a mirror.

9. The spectroscopic microscope of claim 1 wherein the collection elements within the probe head comprises at least one of: a lens, and a CCD camera.

10. The spectroscopic microscope of claim 1 wherein the spectral collection device comprises a Raman spectrometer.

11. The spectroscopic microscope of claim 10 wherein the objective lens comprises an objective lens system situated on a principal axis of the probe head to receive radiation reflected from and emitted by the sample including characteristic Raman spectra produced by the sample and to generate a collimated beam of the radiation aligned with a principal axis of the probe head.

12. The spectroscopic microscope of claim 11 wherein said optical filter is positioned to receive the collimated beam of radiation from the objective lens and allow past primarily only a selected spectral portion including the characteristic Raman spectrum produced from the sample.

13. The spectroscopic microscope of claim 12 wherein said collection elements within the probe head include a lens positioned on the principal axis of the probe head to receive the selected spectral portion passing through the optical filter and direct it toward a focal point, and a spatial filter having an input positioned at about the focal point to receive the selected spectral portion, the spatial filter having an output, the spatial filter attenuating unwanted radiation so that said spectral collection device receives substantially only the characteristic Raman spectrum produced from the sample.

14. A spectroscopic microscope for evaluating a characteristic of a sample, the microscope comprising: a source of spectral energy carried by a fiber optic cable, a probe head coupled to the fiber optic cable and having an objective lens for directing spectral energy from the source toward said sample, optical transmission elements within the probe head defining an optical path between the fiber optic cable and the objective lens, collection elements within the probe head coupled to the objective lens for receiving energy returned from the sample, an optical image collection device coupled to the collection elements for extracting a visual image of the sample, a spectral collection device coupled to the collection elements for extracting a spectral characteristic of the sample, a base adapted to be situated adjacent to the sample, the base including a stand and a support for supporting the stand in a vertical orientation defining a polar axis, and a position controller coupled to the base and the probe head for adjusting the position of the objective lens with respect to the sample including a first angle adjustment means for adjusting the azimuth angle Φ of the probe head relative to the polar axis, the relative position being ascertained at least in part by observation of the visual image of the sample derived from the optical image collection device.

15. The spectroscopic microscope of claim 14 wherein the position controller first angle adjustment means is capable of adjusting the azimuth angle Φ of the probe head relative to the polar axis.

16. The spectroscopic microscope of claim 15 wherein the position controller comprises a second angle adjustment means for adjusting the polar angle Θ of the probe head relative to the base.

17. The spectroscopic microscope of claim 14 wherein the position controller comprises a vertical (Y) adjustment means for adjusting the vertical position of the probe head relative to the base.

18. The spectroscopic microscope of claim 17 wherein the position controller comprises a first horizontal (X) adjustment means for adjusting the horizontal position of the probe head in a first horizontal direction relative to the base.

19. The spectroscopic microscope of claim 18 wherein the position controller comprises a second horizontal (Z) adjustment means for adjusting the horizontal position of the probe head in a second horizontal direction relative to the base.

20. The spectroscopic microscope of claim 14 wherein the optical transmission elements within the probe head defining an optical path between the fiber optic cable and the objective lens comprises at least one of: a spatial filter, a band pass filter, a lens, and a mirror.

21. The spectroscopic microscope of claim 14 wherein the collection elements within the probe head comprises at least one of: a lens, a mirror and a CCD camera.

22. The spectroscopic microscope of claim 14 wherein the spectral collection device comprises a Raman spectrometer.

23. The spectroscopic microscope of claim 22 wherein the objective lens comprises an objective lens system situated on a principal axis of the probe head to receive radiation reflected from and emitted by the sample including characteristic Raman spectra produced by the sample and to generate a collimated beam of the radiation aligned with a principal axis of the probe head.

24. The spectroscopic microscope of claim 23 wherein said collection elements within the probe head include an optical filter positioned to receive the collimated beam of radiation from the objective lens and allow past primarily only a selected spectral portion including the characteristic Raman spectrum produced from the sample.

25. The spectroscopic microscope of claim 24 wherein said collection elements within the probe head include a lens positioned on the principal axis of the probe head to receive the selected spectral portion passing through the optical filter and direct it toward a focal point, and a spatial filter having an input positioned at about the focal point to receive the selected spectral portion, the spatial filter having an output, the spatial filter attenuating unwanted radiation so that said spectral collection device receives substantially only the characteristic Raman spectrum produced from the sample.

26. A spectroscopic microscope for evaluating a characteristic of a sample, the microscope comprising: a source of spectral energy, a probe head having an objective lens for directing spectral energy from the source toward said sample, optical transmission elements within the probe head defining an optical path between the source of spectral energy and the objective lens, collection elements within the probe head coupled to the objective lens for receiving energy returned from the sample, an optical image collection device coupled to the collection elements for extracting a visual image of the sample, a spectral collection device coupled to the collection elements for extracting a spectral characteristic of the sample, a base adapted to be situated adjacent to the sample, the base including a stand and a support for supporting the stand in a vertical orientation defining a polar axis, and a position controller coupled to the base and the probe head for adjusting the position of the objective lens with respect to the sample including a first angle adjustment means for adjusting the azimuth angle $\Phi$ of the probe head relative to the polar axis through a range of at least 45, the relative position being ascertained at least in part by observation of the visual image of the sample derived from the optical image collection device.

27. The spectroscopic microscope of claim 26 wherein the position controller comprises a second angle adjustment means for adjusting the polar angle $\Theta$ of the probe head relative to the base.

28. The spectroscopic microscope of claim 26 wherein the position controller comprises a vertical (Y) adjustment means for adjusting the vertical position of the probe head relative to the base.

29. The spectroscopic microscope of claim 28 wherein the position controller comprises a first horizontal (X) adjustment means for adjusting the horizontal position of the probe head in a first horizontal direction relative to the base.

30. The spectroscopic microscope of claim 29 wherein the position controller comprises a second horizontal (Z) adjustment means for adjusting the horizontal position of the probe head in a second horizontal direction relative to the base.

31. A spectroscopic microscope for evaluating a characteristic of a sample, the microscope comprising: a source of spectral energy, a probe head having an objective lens system situated on a principal axis of the probe head for directing spectral energy from the source toward said sample, the objective lens system receiving radiation reflected from and emitted by the sample including characteristic Raman spectra produced by the sample and generating a collimated beam of the radiation aligned with a principal axis of the probe head, optical transmission elements within the probe head defining an optical path between the source of spectral energy and the objective lens system, collection elements within the probe head coupled to the objective lens for receiving energy returned from the sample, the collection elements including an optical filter positioned to receive the collimated beam of radiation from the objective lens system and allow past primarily only a selected spectral portion including the characteristic Raman spectrum produced from the sample, an optical image collection device coupled to the collection elements for extracting a visual image of the sample, a lens positioned on the principal axis of the probe head to receive the selected spectral portion passing through the optical filter and direct it toward a focal point, and a spatial filter having an input positioned at about the focal point to receive the selected spectral portion, the spatial filter having an output, a spectral collection device coupled to the collection elements for extracting a spectral characteristic of the sample from the output of the spatial filter, the spatial filter attenuating unwanted radiation so that said spectral collection device receives substantially only the characteristic Raman spectrum produced from the sample, a base adapted to be situated adjacent to the sample and a position controller coupled to the base and the probe head for adjusting the position of the objective lens with respect to the sample, the relative position being ascertained at least in part by observation of the visual image of the sample derived from the optical image collection device.

32. The spectroscopic microscope of claim 31 wherein the base comprises a stand and a support for supporting the stand in a vertical orientation defining a polar axis, and wherein the position controller comprises a first angle adjustment means for adjusting the azimuth angle $\Phi$ of the probe head relative to the polar axis.

33. The spectroscopic microscope of claim 32 wherein the position controller comprises a second angle adjustment means for adjusting the polar angle $\Theta$ of the probe head relative to the base.

34. The spectroscopic microscope of claim 32 wherein the position controller comprises a vertical (Y) adjustment means for adjusting the vertical position of the probe head relative to the base.

35. The spectroscopic microscope of claim 32 wherein the position controller comprises a first horizontal (X) adjustment means for adjusting the horizontal position of the probe head in a first horizontal direction relative to the base.

36. The spectroscopic microscope of claim 35 wherein the position controller comprises a second horizontal (Z) adjustment means for adjusting the horizontal position of the probe head in a second horizontal direction relative to the base.

\* \* \* \* \*